United States Patent [19]
Chen

[11] Patent Number: 5,715,837
[45] Date of Patent: Feb. 10, 1998

[54] TRANSCUTANEOUS ELECTROMAGNETIC ENERGY TRANSFER

[75] Inventor: James C. Chen, Bellevue, Wash.

[73] Assignee: Light Sciences Limited Partnership, Issaquah, Wash.

[21] Appl. No.: 705,334

[22] Filed: Aug. 29, 1996

[51] Int. Cl.$^6$ .................................................. A61B 19/00
[52] U.S. Cl. ................................................ 128/899; 600/12
[58] Field of Search .................................. 128/897–899; 600/3, 12, 13; 607/33, 34, 61

[56] References Cited

U.S. PATENT DOCUMENTS

| | | | |
|---|---|---|---|
| 4,829,984 | 5/1989 | Gordon et al. | 600/12 |
| 4,951,675 | 8/1990 | Groman et al. | 600/12 |
| 4,983,159 | 1/1991 | Rand | 600/12 |
| 5,067,952 | 11/1991 | Gudov et al. | 600/12 |
| 5,262,176 | 11/1993 | Palmacci et al. | 600/12 |

*Primary Examiner*—William E. Kamm
*Assistant Examiner*—George R. Evanisko
*Attorney, Agent, or Firm*—Ronald M. Anderson

[57] ABSTRACT

A method and apparatus for enhancing transcutaneous energy transfer to provide power to a medical device that is disposed within the body of a patient. A magnetic field is created by an external transmitting coil (200), which induces an electrical current in a receiving coil (300) that has been placed under the patient's skin (100). The flux path magnetic permeability between the receiving and transmitting coils is enhanced by the implantation of particles (120) into dermis (104) within the skin at that site. The particles, which comprise soft iron or other material having a characteristic high magnetic permeability, are preferably implanted using either a hypodermic needle (150) or a medical air injection device (160). A biocompatible material such as Teflon™ is applied as a coating (123) to the particles. To implant the particles, they are preferably first suspended in a liquid, forming a mixture that is readily delivered to the desired location. The particles are dispersed in a deposit below the epidermis, so that the deposit is between pole faces of the transmitting and the receiving coils. The efficiency of transcutaneous power transfer increases because the magnetic flux density coupling the transmitting and receiving coils is improved by the particles.

13 Claims, 4 Drawing Sheets

TRANSCUTANEOUS ELECTROMAGNETIC ENERGY TRANSFER

FIELD OF THE INVENTION

This invention generally relates to the transfer of electromagnetic energy between a source coil and a receiver coil, and more specifically, to a method and system for improving the efficiency with which electromagnetic power is transcutaneously transferred to energize a medical device implanted within a patient's body.

BACKGROUND OF THE INVENTION

Various types of medical devices such as cochlear implants, artificial hearts, and neural stimulators have been developed that are designed to be surgically inserted within a patient's body to carry out a medically related function for an extended period of time. Although a power lead connected to the implanted device and extending outside the patient's body can be used to supply electrical power required to energize the device, any lead that passes through the skin increases the risk of infection if left in place for more than a few days. Thus, power can be supplied to an implanted medical device from an internal battery pack to avoid this problem. However, any battery used for extended periods of time will eventually need to either be recharged or replaced. Replacing an internally implanted battery subjects the patient to further invasive surgery and is thus not desirable.

An alternative solution to this problem provides for recharging the battery by transcutaneously coupling power from an external source to an implanted receiver that is connected to the battery. Although power can be coupled from an external source at radio frequencies using matching antennas, it is generally more efficient to employ an external transmitter coil and an internal receiving coil that are inductively electromagnetically coupled to transfer power at lower frequencies. In this approach, the external transmitter coil is energized with alternating current (AC), producing a varying magnetic flux that passes through the patient's skin and excites a corresponding AC current in the internal receiving coil. The current in the receiving coil is then typically rectified and filtered for use in charging a battery pack that provides power to the implanted device, but may also be directly applied for powering the implanted device. It should be noted that the receiving coil and any related electronic circuitry may be located at a different point in the patient's body from that at which the implanted device is disposed.

The efficiency with which electromagnetic power is transcutaneously transferred between two coils is a function of the distance between the coils, the design of the coils, including the type of core used for each, the size of the core of each coil, the number of turns of electrical conductor used for each coil, the current flowing through the transmitting coil, and other factors. Air has a relatively poor magnetic permeability characteristic of $m=4p \times 10^{-7}$ Henry/meter, and the magnetic permeability of the dermal layer separating an internal receiving coil from an external transmitting coil is only slightly better. By comparison, the magnetic permeability characteristic of iron is approximately $m=100$ to $600$ Henry/meter. The variation in the magnetic permeability of iron is inversely proportional to the density of the magnetic flux. Thus, transcutaneous electromagnetic power transfer between two coils is relatively inefficient compared to the efficiency that could be achieved if the two coils were coupled by a material such as iron, having a superior magnetic permeability.

Clearly, it is desirable to limit the amount of time required for inductively coupling electrical power to charge an internal battery supply used to energize an implanted device. Similarly, it would be desirable to improve the efficiency with which power is coupled to an implanted device that is directly energized by transcutaneously transferred power. The time required to charge a battery pack is generally proportional to the efficiency of the inductive coupling process. In addition, due to miniaturization of the receiving coil used in certain types of implanted devices, it is very important to optimize the inductive coupling between the external transmitter coil and the receiving coil connected to the internal device, particularly when the device is directly energized. Design changes in the transmitter and receiver coils are likely only to achieve a minimal improvement in the efficiency of the power transfer process. Further enhancements to the efficiency of the process will require a different approach.

SUMMARY OF THE INVENTION

The present invention is directed to a method for enhancing transcutaneous energy transfer that is used to provide electrical power to a medical device implanted within a patient's body. Transcutaneous energy transfer employs a transmitting coil that is disposed externally, generally in contact with a patient's skin and positioned directly over or opposite a receiving coil that has been implanted within the patient's body. The external transmitting coil produces a magnetic field that induces a current in the internal receiving coil, which is used to supply energy for the implanted medical device.

The magnetic permeability of tissue is low, so that the coupling between the external transmitting coil and the internal receiving coil is relatively poor. The present invention addresses this problem by improving the coupling between the transmitting and receiving coils. In the invention, a plurality of particles having a characteristic relatively high magnetic permeability are implanted in the patient's body, above the internal receiving coil and under the top surface of the patient's skin. These particles improve the transfer of electromagnetic energy by enhancing the magnetic permeability of the flux path between the transmitting and receiving coils.

Materials such as soft iron, permalloy, mu metal alloy, and supermalloy comprise a core of each of the particles, and the core is coated with a protective biocompatible layer. This layer can be manufactured in various colors to selectively cosmetically mask the particles, minimizing their visibility through the skin, or alternatively, to enhance the visibility of the particles, making it easier to locate the internal receiving coil that lies under the particles. Each particle has a size within the range from about 50 micrometers to about one millimeter.

A further aspect of the present invention is directed to a method for implanting a plurality of such particles at a site within the patient's body. Preferably, the particles are added to a liquid so that they are suspended, forming a mixture. The mixture is then injected into the patient's body, using a hypodermic needle or an air injection gun. Alternatively, a plurality of small incisions may be made in the patient's skin and the particles implanted in the incisions.

BRIEF DESCRIPTION OF THE DRAWING FIGURES

The foregoing aspects and many of the attendant advantages of this invention will become more readily appreciated

3 as the same becomes better understood by reference to the following detailed description, when taken in conjunction with the accompanying drawings, wherein:

DESCRIPTION OF THE PREFERRED EMBODIMENT

Figure 2:
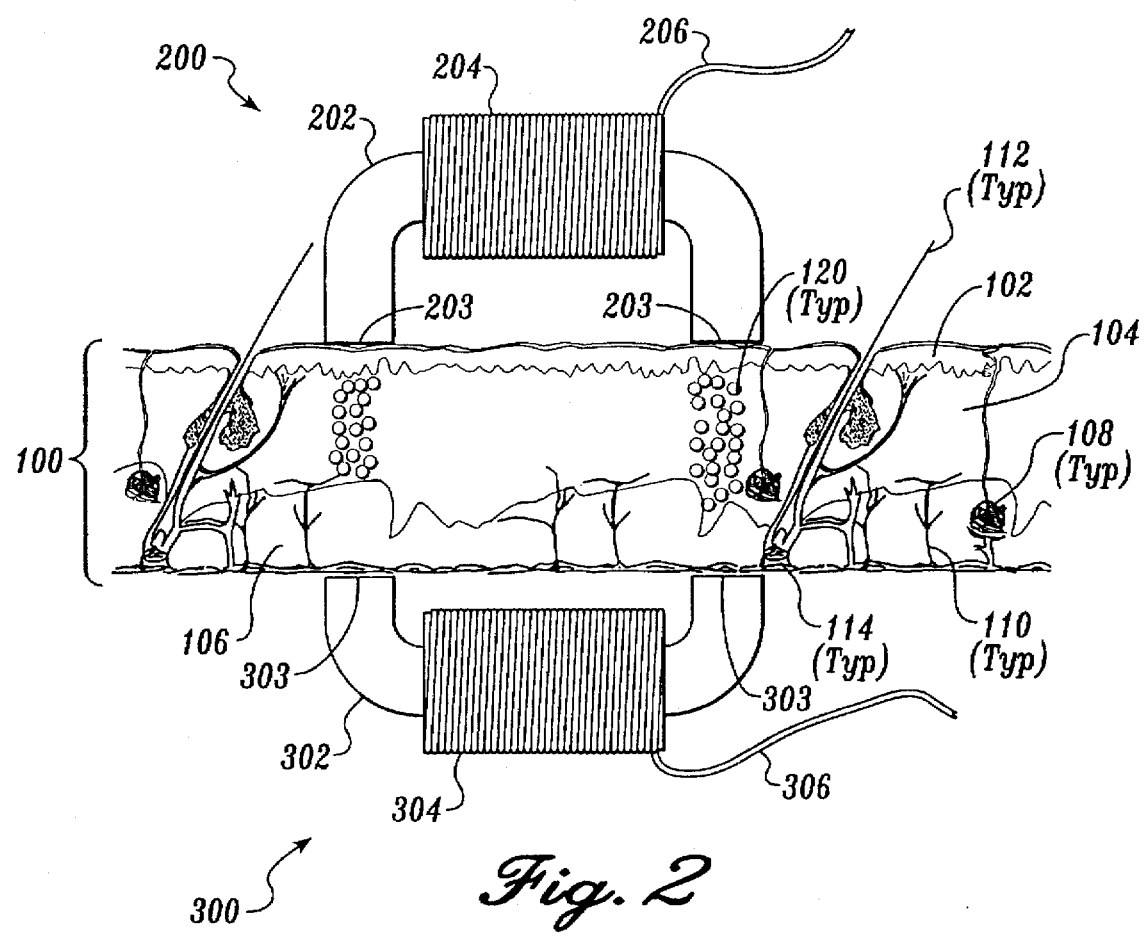
FIG. 2 is a side section view of skin containing implanted particles having a relatively high magnetic permeability in accord with the present invention and illustrating a transmitter coil and a receiving coil that couple power transcutaneously through a path comprising the particles.

A first embodiment of a technique to improve transcutaneous energy transfer to a medical device (not shown) that has been implanted within a patient's body is illustrated in FIG. 2. The human body is protected by a layer of skin 100, generally comprising a top layer or epidermis 102, and a bottom layer or dermis 104. The skin is part of a very complex group of organs collectively referred to as the integumentary system. Also included within this system are hair follicles 114, sweat glands 108, and capillary blood vessels 110. The skin borders an internal layer of subcutaneous tissue or hypodermis 106. Hypodermis 106 anchors skin 100 to the underlying structure of the body, yet allows the skin to move relative to the body.

Although the magnetic permeability of the integumentary system is slightly better than air, it is still relatively poor, which substantially limits the efficiency with which electromagnetic power can be transferred transcutaneously. It will be recalled from the discussion in the Background of the Invention that transcutaneous energy transfer provides means for coupling power from an external source to an internally disposed medical device that has been surgically implanted within the body of a patient. The present invention greatly improves the efficiency with which power is transmitted transcutaneously for this purpose.

As illustrated in FIG. 2, an external transmitting coil 200 is illustrated in contact with epidermis 102, generally opposite a receiving coil 300, which has been surgically or endoscopically implanted below hypodermis 106. Transmitting coil 200 comprises a winding 204, a core 202, and wire leads 206. Wire leads 206 are connected to an external power supply that provides an AC voltage, forcing a substantial current to flow through winding 204, so that a corresponding AC magnetic field is produced by transmitting coil 200. It will be apparent that winding 204 could also be energized with a pulsating DC voltage.

Receiving coil 300 comprises a winding 304, a core 302, and wire leads 306. Wire leads 306 are used to transfer current induced in winding 304 to the remotely disposed medical device that is implanted within the patient's body. The current induced in winding 304 can be used directly to power the device or can be rectified and applied to charging a battery that normally provides power to the implanted device. Details of the medical device circuitry are not illustrated in the drawings nor described in this disclosure, since such details are irrelevant to the present invention.

The transmitting coil has a winding wrapped around a generally U-shaped core. The receiving coil similarly includes a winding wrapped around a generally U-shaped core. The windings are wrapped around each core in concentric layers (not separately shown). The magnetic flux density within core 202 of transmitting coil 200 is dependent upon the magnetic permeability characteristics of transmitting core 202, the number of turns of conductor comprising winding 204, and the magnitude of the current flowing through winding 204. The materials comprising core 202 and core 302 are selected because of their characteristic high magnetic permeability to optimize the magnetic flux density within the cores. Core 202 directs and focuses the magnetic flux from winding 204 out through pole faces 203, which are disposed at opposite ends of the core. On receiving coil 300, opposite ends of core 302 comprise pole faces 303 that receive the magnetic flux produced by transmitting coil 200 and direct the flux through the core of receiving coil 300. The magnetic flux within core 302 causes an electrical current to be induced in winding 304 that is proportional to the intensity of the magnetic flux within the core, and to the number of turns of the conductor comprising winding 304. However, the amount of power transferred to receiving coil 300 to produce the flux within core 302 is directly proportional to the magnetic permeability of the material between pole faces 203 and 303.

Power transfer between the transmitting coil and the receiving coil can be improved in two ways. First, the magnitude of the magnetic flux produced by the transmitting coil can be increased, e.g., by increasing the current flowing in the windings of the transmitting coil. However, a higher current requires physically larger windings, i.e., more turns of the conductor comprising the winding, and may require a larger gauge conductor to safely carry the higher current. There is a practical limit to the size of the transmitting coil used for this purpose. A second way to improve power transfer is to increase flux density coupling between the facing pole faces of the transmitting and receiving coils. The flux density can be increased by increasing the magnetic permeability of the material comprising the physical barrier separating the pole faces of the transmitting coil from the pole faces of the receiving coil. The second technique increases the efficiency of power transfer without requiring any modification of the transmitting and receiving coils or any changes in the power supply or current that energizes transmitting coil 200. The present invention is thus directed to increasing the magnetic permeability of the tissue separating transmitting coil 200 and receiving coil 300 to improve the efficiency with which electromagnetic energy is transferred between the two coils.

To improve the magnetic permeability of skin or other tissue disposed between the transmitting and receiving coils, magnetically permeable particles 120 are implanted within the tissue of a patient's body at that site so that the particles lie between the pole faces of the two coils. To facilitate their implantation at the site, particles 120 are preferably added to a saline solution or other biocompatible liquid to form a mixture in which the particles are at least initially suspended. The mixture is then drawn into a delivery device and the delivery device is positioned on the top surface of skin 100, at the site overlying receiving coil 300. Using the delivery device, the mixture is forced into dermis 104 at the site. These steps are repeated as necessary to achieve a desired density of particles 120 beneath epidermis 102, and create a generally uniform distribution of the particles, at least overlying pole faces 303 of receiving coil 300.

Figure 3:
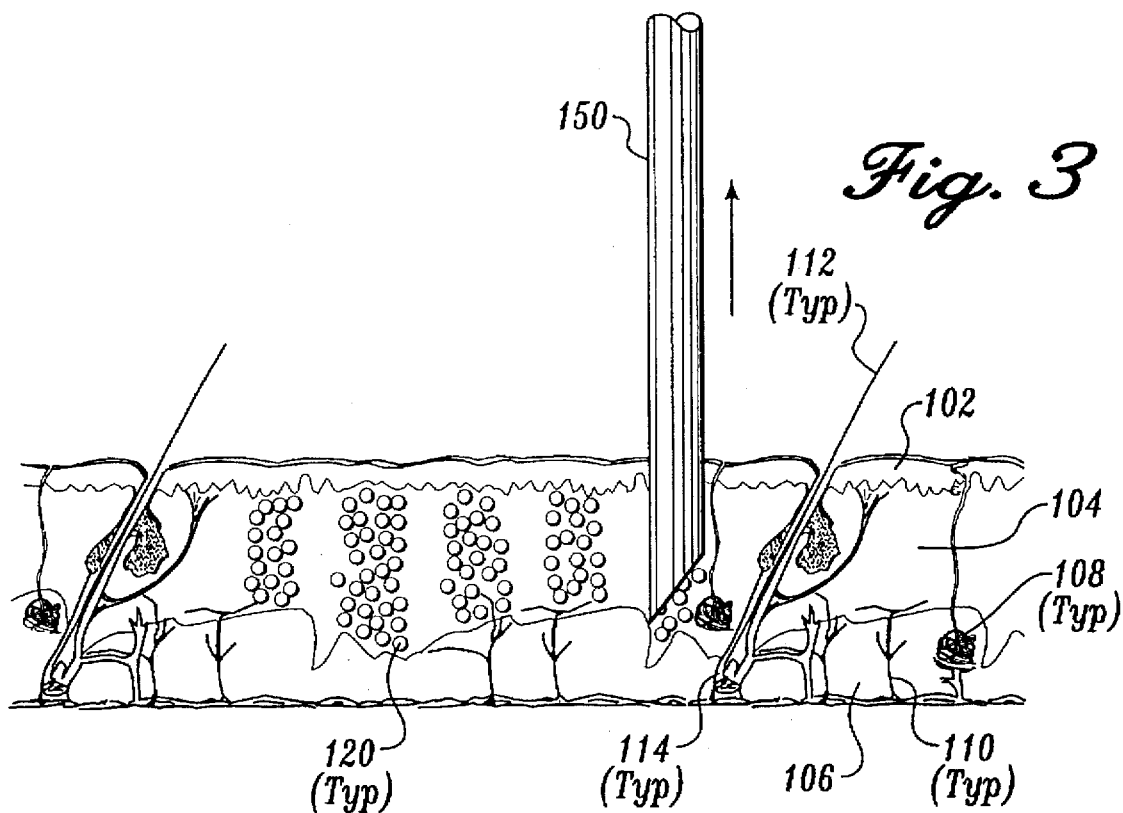
FIG. 3 is a side sectional view of skin showing a hypodermic needle inserted into the skin and showing the deposition of the particles in the dermis as the needle is withdrawn.
Figure 4:
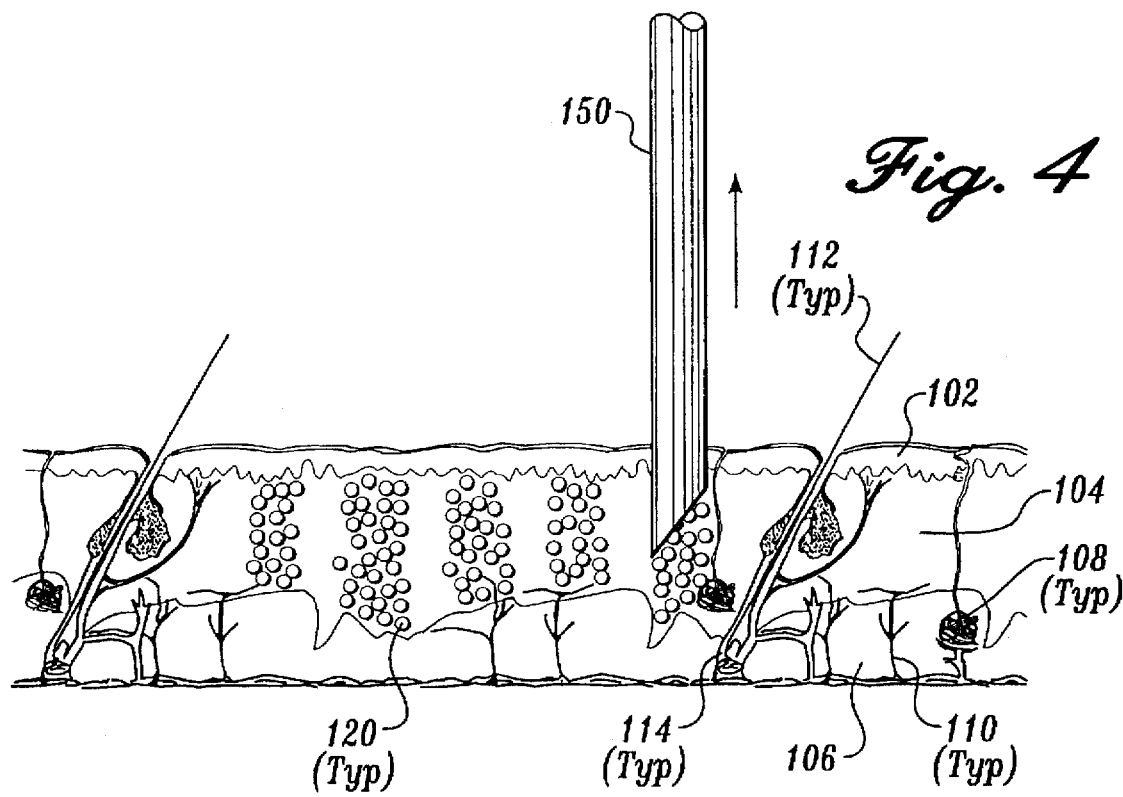
FIG. 4 is a side sectional view of the skin showing the needle further withdrawn (compare to FIG. 3) as the particles are injected.

In FIG. 3, a hypodermic needle 150 is illustrated as the delivery device used to implant particles 120 at the site. Hypodermic needle 150 is shown after it has been inserted through epidermis 102 and into dermis 104. The tip of the needle rests just above hypodermis 106 and the particles are being injected through the needle as it is withdrawn from the dermis. In FIG. 4, hypodermic needle 150 is shown partially withdrawn from dermis 104, leaving behind a columnar deposit of particles 120. These particles are deposited within the column at a substantially uniform density. The implanted particles have a characteristic magnetic permeability that is substantially greater than skin and thus greatly improves the efficiency of transcutaneous electromagnetic power transfer between the transmitting coil and receiving coil.

Figure 1:
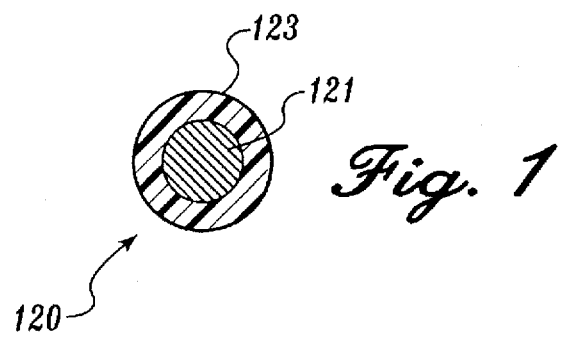
FIG. 1 is a cross-sectional view of one of the particles of the present invention, showing a biocompatible coating around a core.

As shown in FIG. 1, each particle 120 comprises a core 121 of a material such as soft iron, permalloy, mu metal alloy, or supermalloy having a characteristic high magnetic permeability. A coating 123 of a biocompatible material such as one of the polyurethane or TEFLON™ compounds typically used for coating medical implants is applied to the particle core. Particles 120 are substantially spherical, and can have a diameter from about 50 micrometers to about 1 millimeter. Since epidermis 102 is relatively translucent, particles 120 may discolor the skin at the site of their implantation, possibly causing it to appear a mottled gray color. However, by coloring coating 123 various appropriate flesh colors, particles 120 may be made to cosmetically blend with the skin of the patient. This option is further discussed below.

Figure 5:
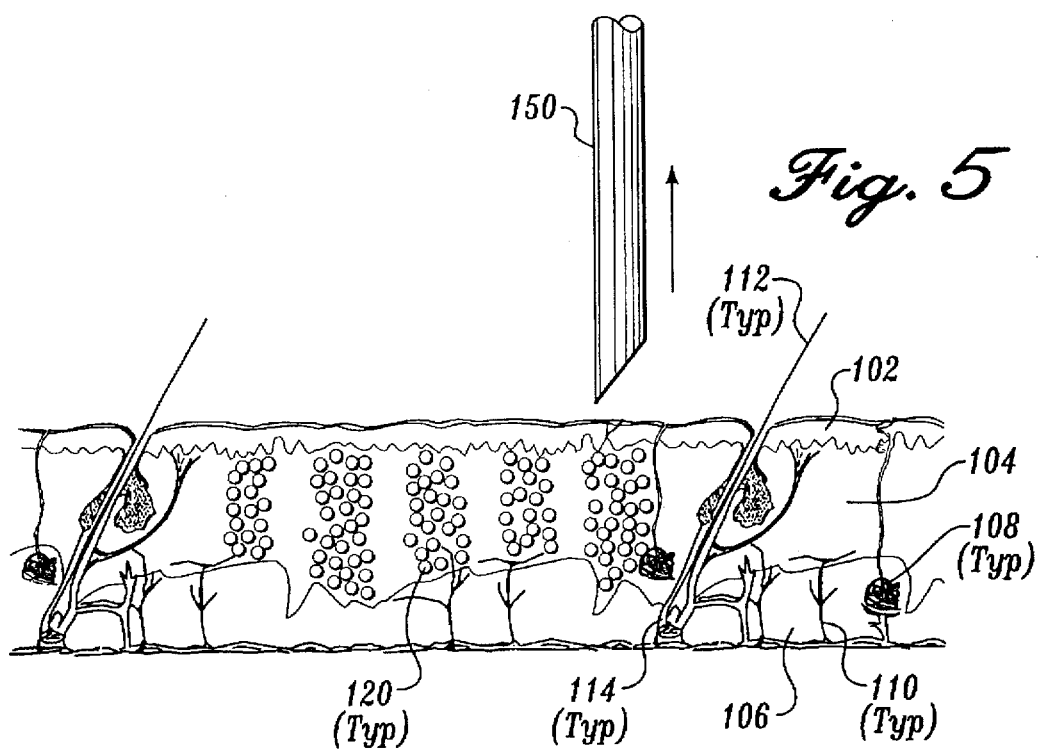
FIG. 5 is a side sectional view of the skin with a needle positioned above the top surface of the skin and showing the particles deposited within the skin.

Referring now to FIG. 5, hypodermic needle 150 is illustrated positioned above epidermis 102 after it has been used to implant multiple columnar deposits of particles 120 within dermis 104. The resulting multiple columnar deposits of particles implanted beneath epidermis 102 are generally analogous to the dye pigment deposits introduced into the dermis when creating a tattoo. A tattoo artist employs a needle to inject multiple colored pigment clusters, having diameters of approximately 140 to 180 micrometers, beneath the top surface of the skin. The deposits of dye pigment define the tattoo. Similarly, in the present invention, a particular area of skin located above a receiving coil is injected with multiple deposits of particles 120, and the particles are generally analogous to the colored pigment clusters of a tattoo. However, epidermis 102 is relatively translucent and a patient treated with the present invention may prefer that the introduction of particles 120 not change the appearance of the skin. In other cases, it may be preferable that the implanted particles be clearly visible to facilitate accurately positioning transmitting coil 200 against epidermis 102, immediately opposite receiving coil 300. Thus, the color of coming 123 on particles 120 may be selected to either enhance or reduce the extent to which the particles are visible through epidermis 102.

Figure 6:
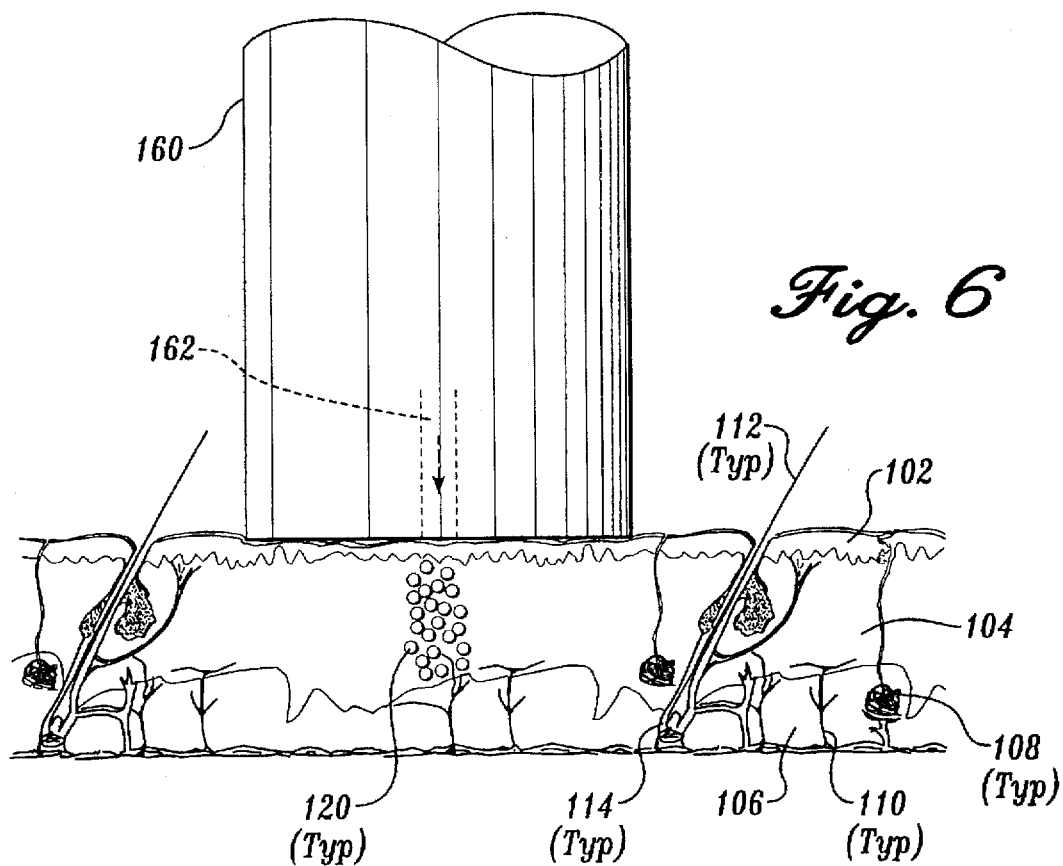
FIG. 6 is a side sectional view of the skin with a medical air injection nozzle positioned against the top surface of the skin and showing the result of having uniformly deposited magnetically permeable particles within the skin by air injection.

An alternative method for implanting particles 120 is illustrated in FIG. 6. In this Figure, a medical air injection nozzle 160 having an injection channel 162 is shown positioned above a columnar deposit of particles 120 that have been injected into the dermis using the device. The air injection nozzle employs pressurized air to force a plurality of particles 120 through epidermis 102, producing a columnar deposit of particles 120 within dermis 104. One advantage of the air injection nozzle method for implanting the particles is the capacity of this device to deliver a generally uniform density of implanted particles with each injection. In contrast, the columnar deposit density can vary between columns when a hypodermic needle is employed to implant particles 120. The density of the particles injected using a hypodermic needle is dependent upon the pressure applied by a particular individual against a plunger of the syringe (not shown) and the rate at which the needle is withdrawn as the injection is delivered, both of which can vary.

Figure 7:
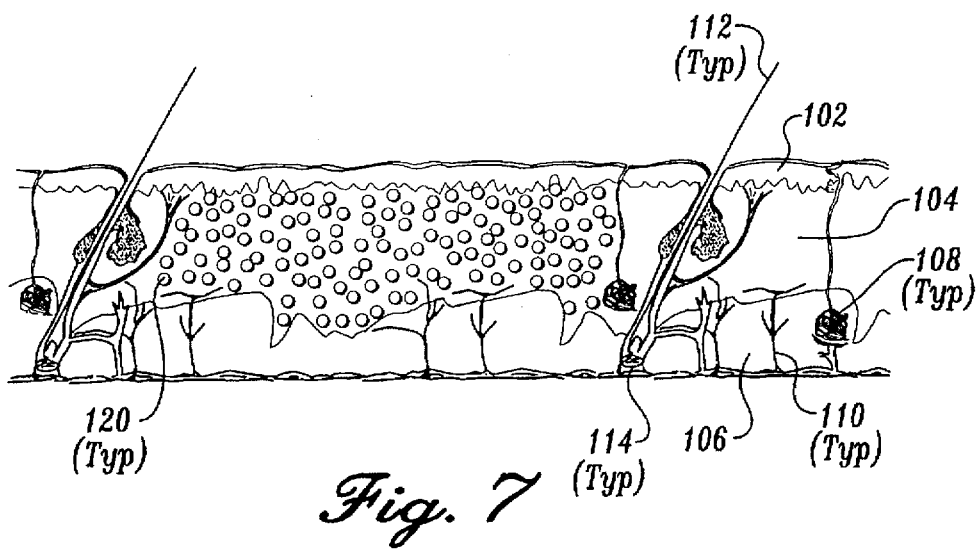
FIG. 7 is a side sectional view of the skin, showing a heavy deposit of particles within the skin.
Figure 8:
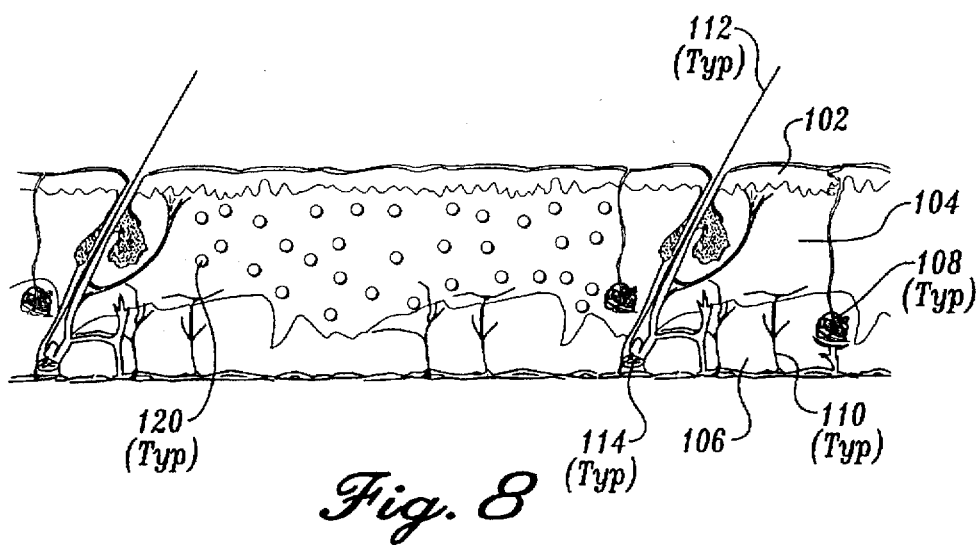
FIG. 8 is a side sectional view of the skin, showing a light deposit of the particles within the skin.
Figure 9:
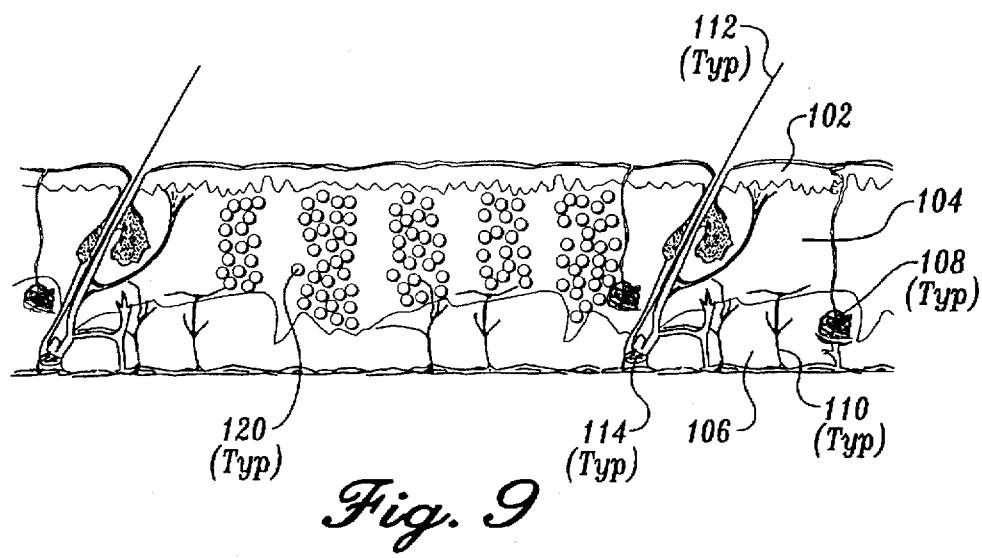
FIG. 9 is a side sectional view of the skin, showing a columnar deposit of the particles within the skin.

Particles 120 can be implanted within tissue in various selected densities. For example, referring to FIG. 7, a uniform high density deposit of particles 120 is shown implanted beneath epidermis 102. In FIG. 8, a uniform light density deposit of particles 120 is shown, and in FIG. 9, multiple columnar high density deposits of particles 120 are illustrated. Typically, a medical practitioner would select an appropriate density deposit of particles 120 for use with a specific patient, to provide a required magnetic flux density for the transfer of electromagnetic energy from transmitting coil 200 to receiving coil 300. Various parameters that may determine the density of the particles used with a specific patient include the power requirement of the medical device being energized, the thickness of skin 100 at the site selected, the size of the implanted receiver coil, the electrical current supplied to the transmitting coil, the size of the transmitting coil, (i.e., the number of turns of conductor used for winding 204), and the distribution of the flux pattern.

As an alternative to injecting the particles using a needle or air injection nozzle, as described above, it is also contemplated that a plurality of small incisions can be made through epidermis 102 and into dermis 104 at the site overlying receiving coil 300. The particles can then be implanted within the pockets formed by the incisions, using a small catheter or other appropriate tools, leaving a columnar deposit of the particles at each small incision.

It is also contemplated that the present invention can be employed in connection with the implantation of particles within bones and/or tissue at other sites within the body to improve the magnetic permeability, which couples a transmitting coil and receiving coil and the power transferred between the two coils. To reach implantation sites deep within a patient's body, a longer hypodermic needle could be employed or the site could be surgically exposed to facilitate the injection of the particles using an air injection nozzle or needle.

Although the present invention has been described in connection with several preferred forms of practicing it, those of ordinary skill in the art will understand that many other modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for enhancing transcutaneous energy transfer from an external source to a receiver implanted within a body to energize a medical device disposed within the body, comprising the steps of:

(a) providing a plurality of particles comprising a material having a characteristic magnetic permeability substantially greater than that of tissue in the body; and (b) implanting the plurality of particles at a site within the tissue of the body so that the plurality of particles are dispersed in a spaced-apart array, said plurality of particles comprising an enhanced flux path between the external source and the receiver for transferring electromagnetic energy through the tissue at said site and thereby adapted to energize the medical device.

2. The method of claim 1, wherein each of the plurality of particles further comprises a biocompatible coating.

3. The method of claim 2, wherein the biocompatible coating is colored to either make the biocompatible coating more or less visible relative to a patient's skin color.

4. The method of claim 1, wherein the step of implanting includes the step of mixing the plurality of particles into a liquid to form a mixture.

5. The method of claim 4, wherein the step of implanting further comprises the step of injecting the mixture into the tissue at said site.

6. The method of claim 4, wherein the step of implanting further comprises the step of injecting the mixture into the tissue at said site using an air gun.

7. The method of claim 4, wherein the step of implanting further comprises the step of injecting the mixture into the tissue at said site using a needle.

8. The method of claim 1, further comprising the step of making a plurality of incisions in the tissue adjacent to the site and implanting the plurality of particles in the plurality of incisions.

9. The method of claim 1, wherein each of the plurality of particles has a size within the range from about 50 micrometers to about one millimeter.

10. The method of claim 1, wherein the step of implanting further comprises the step of disposing the plurality of particles within the tissue in a plurality of spaced-apart columns.

11. A method for enhancing transcutaneous energy transfer within a body, comprising the steps of:

(a) providing a plurality of particles comprising a material having a characteristic magnetic permeability substantially greater than that of tissue in the body, said plurality of particles each including a biocompatible coating; and (b) implanting the plurality of particles at a site within the tissue of the body so that the plurality of particles are dispersed in a spaced-apart array, said plurality of particles comprising an enhanced flux path for transferring electromagnetic energy through the tissue at said site.

12. A method for enhancing transcutaneous energy transfer within a body, comprising the steps of:

(a) providing a plurality of particles comprising a material having a characteristic magnetic permeability substantially greater than that of tissue in the body, each of said plurality of particles including a biocompatible coating that is colored to either make the biocompatible coating more or less visible relative to a patient's skin color; and (b) implanting the plurality of particles at a site within the tissue of the body so that the plurality of particles are dispersed in a spaced-apart array, said plurality of particles comprising an enhanced flux path for transferring electromagnetic energy through the tissue at said site.

13. A method for enhancing transcutaneous energy transfer within a body, comprising the steps of:

(a) providing a plurality of particles comprising a material having a characteristic magnetic permeability substantially greater than that of tissue in the body; and (b) implanting the plurality of particles at a site within the tissue of the body so that the plurality of particles are dispersed in a spaced-apart array comprising a plurality of spaced-apart columns, said plurality of spaced-apart columns comprising an enhanced flux path or transferring electromagnetic energy through the tissue at said site.

* * * * *

UNITED STATES PATENT AND TRADEMARK OFFICE
CERTIFICATE OF CORRECTION

PATENT NO. : 5,715,837
DATED : February 10, 1998
INVENTOR(S) : James C. Chen

It is certified that error appears in the above-indentified patent and that said Letters Patent is hereby corrected as shown below:

Location

Column 5, line 65      "coming 123" should read --coating 123--

Column 8, line 36, (Claim 13)      "or" should read --for--

Signed and Sealed this

Twenty-third Day of June, 1998

Attest:

BRUCE LEHMAN

Attesting Officer      *Commissioner of Patents and Trademarks*